(12) United States Patent
Kato et al.

(10) Patent No.: US 8,741,339 B2
(45) Date of Patent: Jun. 3, 2014

(54) ACTIVE TARGETING POLYMER MICELLE ENCAPSULATING DRUG, AND PHARMACEUTICAL COMPOSITION

(75) Inventors: Yasuki Kato, Chiba (JP); Mitsunori Harada, Chiba (JP); Hiroyuki Saito, Chiba (JP); Tatsuyuki Hayashi, Chiba (JP)

(73) Assignee: Nonocarrier Co., Ltd., Chiba (JP)

( * ) Notice: Subject to any disclaimer, the term of this patent is extended or adjusted under 35 U.S.C. 154(b) by 187 days.

(21) Appl. No.: 12/672,496

(22) PCT Filed: Jul. 29, 2009

(86) PCT No.: PCT/JP2009/063838
§ 371 (c)(1),
(2), (4) Date: Apr. 20, 2010

(87) PCT Pub. No.: WO2010/013836
PCT Pub. Date: Feb. 4, 2010

(65) Prior Publication Data
US 2010/0221320 A1    Sep. 2, 2010

(30) Foreign Application Priority Data
Jul. 29, 2008    (JP) ................. 2008-194825

(51) Int. Cl.
*A61K 47/48*    (2006.01)
*A61K 9/10*    (2006.01)

(52) U.S. Cl.
USPC ........................................................ 424/451

(58) Field of Classification Search
None
See application file for complete search history.

(56) References Cited

U.S. PATENT DOCUMENTS

| | | | | |
|---|---|---|---|---|
| 2002/0197261 A1* | 12/2002 | Li et al. | ...................... | 424/178.1 |
| 2006/0240092 A1* | 10/2006 | Breitenkamp et al. | ......... | 424/450 |
| 2007/0253899 A1* | 11/2007 | Ai et al. | ...................... | 424/1.37 |
| 2008/0248097 A1* | 10/2008 | Kwon et al. | .................. | 424/450 |
| 2009/0074874 A1* | 3/2009 | Amano et al. | ................ | 424/497 |

FOREIGN PATENT DOCUMENTS

| EP | 1878766 A1 * | 1/2008 |
|---|---|---|
| EP | 2077293 A1 | 7/2009 |
| JP | 2007-119436 A | 5/2007 |
| WO | WO 02/087497 A2 | 11/2002 |
| WO | WO 2007/048121 A2 | 4/2007 |
| WO | WO 2007/066781 A1 | 6/2007 |
| WO | WO 2008/047948 A1 | 4/2008 |

OTHER PUBLICATIONS

Kensuke Osada, R. James Christie and Kazunori Kataoka. Polymeric micelles from poly(ethylene glycol)-poly(amino acid) block copolymer for drug and gene delivery. J. R. Soc. Interface Jun. 6, 2009 vol. 6 No. Suppl 3 S325-S339.*

Yokoyama M, Miyauchi M, Yamada N, Okano T, Sakurai Y, Kataoka K, Inoue S. Characterization and anticancer activity of the micelle-forming polymeric anticancer drug adriamycin-conjugated poly(ethylene glycol)-poly(aspartic acid) block copolymer. Cancer Res. Mar. 15, 1990;50(6):1693-700.*

Yasuhiro Matsumura. Polymeric Micellar Delivery Systems in Oncology. Japanese Journal of Clinical Oncologyvol. 38, Issue 12pp. 793-802.*

Susan E. Matthews, Colin W. Pouton, and Michael D. Threadgill. Macromolecular systems for chemotherapy and magnetic resonance imaging. Advanced Drug Delivery Reviews vol. 18, Issue 2, Jan. 15, 1996, pp. 219-267.*

Yong-kyu Lee. Preparation and Characterization of Folic Acid Linked Poly(L-glutamate) Nanoparticles for Cancer Targeting. Macromolecular Research, vol. 14, No. 3, pp. 387-393 (2006).*

Kazunori Kataoka, Atsushi Haradaa and Yukio Nagasaki. Block copolymer micelles for drug delivery: design, characterization and biological significance. Advanced Drug Delivery Reviews vol. 47, Issue 1, Mar. 23, 2001, pp. 113-131.*

Vega J, Ke S, Fan Z, Wallace S, Charsangavej C, Li C. Targeting doxorubicin to epidermal growth factor receptors by site-specific conjugation of C225 to poly(L-glutamic acid) through a polyethylene glycol spacer. Pharm Res. May 2003;20(5):826-32.*

Norased Nasongkla, Erik Bey, Jimin Ren, Hua Ai, Chalermchai Khemtong, Jagadeesh Setti Guthi, Shook-Fong Chin, A. Dean Sherry, David A. Boothman, and Jinming Gao. Multifunctional Polymeric Micelles as Cancer-Targeted, MRI-Ultrasensitive Drug Delivery Systems. Nano Lett., 2006, 6 (11), pp. 2427-2430.*

Taiho Noh, Yeon Hee Kook, Chiyoung Park, Hyewon Youn, Hana Kim, Eun Tax Oh, Eun Kyung Choi, Heon Joo Park, Chulhee Kim. Block Copolymer Micelles Conjugated with anti-EGFR Antibody for Targeted Delivery of Anticancer Drug. Journal of Polymer Science: Part A: Polymer Chemistry v.46, 7321-7331 (2008).*

(Continued)

*Primary Examiner* — Robert A Wax
*Assistant Examiner* — Olga V Tcherkasskaya
(74) *Attorney, Agent, or Firm* — J-TEK LAW PLLC; Jeffrey D. Tekanic (57) ABSTRACT

The present invention provides an active targeting polymer micelle encapsulating a drug, preventing an inappropriate release of a drug which may damage a normal cell. A polymer micelle 100 includes a backbone polymer unit 10 that has a target binding site 11 and a backbone polymer unit 20 that has a drug 14 and is free from the target binding site 11, such polymer units 10 and 20 being disposed in a radial arrangement in a state where the target binding site 11 is directed outward and the drug 14 is directed inward, in which: i) when the micelle is bound to a target 40 while maintaining the radial arrangement, the micelle is taken up into a cell 50 supplying the target 40 through endocytosis, and the drug 14 is released into the cell 50 by collapse of the radial arrangement in the cell 50; and ii) when the radial arrangement collapses in blood 60 before the micelle is bound to a target 40, the unit 20 is excreted through metabolism, to thereby prevent a normal cell from being damaged by the drug 14.

21 Claims, 6 Drawing Sheets

(56) References Cited

OTHER PUBLICATIONS

Bae Y, Nishiyama N, Kataoka K. In vivo antitumor activity of the folate-conjugated pH-sensitive polymeric micelle selectively releasing adriamycin in the intracellular acidic compartments. Bioconjug Chem. Jul.-Aug. 2007;18(4):1131-9.*

Hyuk Sang Yoo, Tae Gwan Park. Folate receptor targeted biodegradable polymeric doxorubicin micelles. J Control Release. Apr. 28, 2004;96(2):273-83.*

Asahina et al. (2006) "A Phase II Trial of Gefitinib as First-Line Therapy for Advanced Non-Small Cell Lung Cancer with *Epidermal Growth Factor Receptor* Mutations" British Journal of Cancer 95:998-1004.

International Search Report Translation Sep. 1, 2009 in English.

International Search Report and Written Opinion mailed Sep. 1, 2009 in Japanese.

Extended European Search Report dated Jun. 17, 2011, issued in corresponding EP Patent Application No. 09803068.7.

Bae et al (2007) "In Vivo Antitumor Activity of the Folate-Conjugated pH-Sensitive Polymeric Micelle Selectively Releasing Adriamycin in the Intracellular Acidic Compartments" Bioconjugate Chem. 18:1131-1139.

N. Nishiyama et al., Preparation and Characterization of Self-Assembled Polymer-Metal Complex Micelle from cis-Dichlorodiammineplatinum(II) and Poly(ethylene glycol)-Poly($\alpha,\beta$-aspartic acid) Block Copolymer in an Aqueous Medium, Langmuir, 15 (1999), pp. 377-383.

Y. Ogawa, Injectable microcapsules prepared with biodegradable poly($\alpha$-hydroxy) acids for prolonged release of drugs, J. Biomater. Sci. Polymer Edn, vol. 8 (1997), No. 5, pp. 391-409.

Examination Report dated Jun. 14, 2012 for counterpart EP application No. 09 803 068.7-1216 with examined claims 1-4.

Y. Jeong et al., Cellular recognition of paclitaxel-loaded polymeric nanoparticles composed of poly($\gamma$-benzyl L-glutamate) and poly(ethylene glycol) diblock copolymer endcapped with galatose moiety, International Journal of Pharmaceutics, 296 (2005), pp. 151-161.

* cited by examiner

ACTIVE TARGETING POLYMER MICELLE ENCAPSULATING DRUG, AND PHARMACEUTICAL COMPOSITION

TECHNICAL FIELD

The present invention relates to an active targeting polymer micelle encapsulating a drug, which is directed to a dosing target such as a tumor cell, an inflammatory cell, an immunocompetent cell, a neovessel, and a vascular endothelium, and a pharmaceutical composition utilizing the micelle.

BACKGROUND ART

When a drug is systemically administered through an oral route and by an intravenous injection, the drug is supplied to not only a focal site as a dosing target but also to normal tissue. As a result, adverse side effects due to the drug administration are observed, and in some cases, the therapeutic method must be changed or discontinued. In order to reduce adverse side effects, a drug referred to as a molecular target drug having a specific binding ability to a molecular marker such as a receptor, a ligand, and an enzyme peculiar to a dosing target has been developed (see H Asahina, et al., "A phase II trial of gefitinib as first-line therapy for advanced non-small cell lung cancer with epidermal growth factor receptor mutations", British Journal of Cancer (2006) 95, pp. 998-1004). However, at present, such a molecular target drug has not been able to sufficiently reduce adverse side effects such as the occurrence of interstitial pneumonitis caused by the administration of gefitinib, and further, does not exhibit a sufficient therapeutic effect at the focal site.

In order to specifically supply a drug to a dosing target and maintain an optimum drug concentration in the vicinity of the dosing target, a technology referred to as a drug delivery system (DDS) is attracting attention. WO 2002/087497 discloses an active targeting polymer conjugate DDS in which a drug and a ligand are bound to a synthetic polymer.

SUMMARY OF THE INVENTION

In order to reduce adverse side effects, a drug that has not been properly delivered to a dosing target is preferably expelled from the body before damaging a normal cell. In the polymer conjugate as described in WO 2002/087497, a drug and a ligand are bound to one synthetic polymer chain. Hence, when the polymer conjugate is bound to a corresponding receptor but is not taken up into a cell as a dosing target, the drug is continuously exposed to blood. Thus, such conventional active targeting DDS still leaves room for improvement in order to reduce adverse side effects.

The present invention provides an active targeting polymer micelle encapsulating a drug, including a backbone polymer unit α that has a target binding site and a backbone polymer unit β that has a drug and is free from the target binding site, the backbone polymer unit α and the backbone polymer unit β being disposed in a radial arrangement in a state where the target binding site is directed outward and the drug is directed inward, in which: i) when the micelle is bound to a target while maintaining the radial arrangement, the micelle is taken up into a cell supplying the target through endocytosis, and the drug is released into the cell by collapse of the radial arrangement in the cell; and ii) when the radial arrangement collapses in blood before the micelle is bound to a target, the backbone polymer unit β is excreted through metabolism, to thereby prevent a normal cell from being damaged by the drug.

In the present specification, the target binding site contained in the backbone polymer unit α means a site that has a biological recognition function of being able to specifically bind to a substance derived from a living body and a virus and form a biological bonding pair with the substance. Examples of the substance derived from a living body and a virus include molecules present in a living cell, a bacterium, a fungus, and a virus. Examples of the living cell include a tumor cell and a neovascular cell and their marginal cells, an immunocompetent cell (for example, a B cell), an inflammatory cell (for example, a leukocyte), a vascular endothelial cell, and cells forming various organs. The backbone polymer unit α may contain a target binding site by incorporating compounds such as a protein, a peptide, and a sugar chain each forming a bonding pair with such substance.

In another aspect of the present invention, there is provided a pharmaceutical composition containing the above-mentioned polymer micelle and a pharmaceutically acceptable carrier.

In the present invention, by incorporating a drug and a target binding site into separate polymer units, a micelle has been provided with a safety mechanism that can eliminate a drug from the body through metabolism when a micelle structure collapses before the micelle is taken up into a cell as a dosing target. As a result, the occurrence of adverse effects is more easily avoided compared with a conventional active targeting DDS.

Figure 6A:
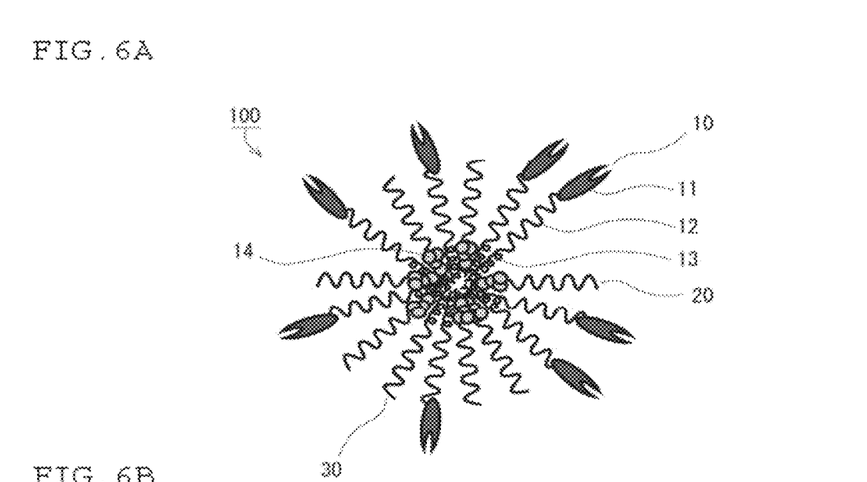
FIGS. 6A to 6C are each a conceptual diagram for explaining a structure and an action of the polymer micelle of the present invention.

As shown in FIG. 6A, a polymer micelle 100 according to an embodiment of the present invention has a backbone polymer unit α 10 and a backbone polymer unit β 20. The backbone polymer unit α 10 has a residue of a compound having a target binding site 11, a hydrophilic polymer segment 12 typified by a polyethylene glycol chain, and a hydrophobic polymer segment 13 typified by a polyamino acid chain. Polyethylene glycol may be referred to as PEG. The target binding site 11 is bound to the hydrophilic polymer segment 12. The backbone polymer unit β 20 has a drug 14, the hydrophilic polymer segment 12 typified by a polyethylene glycol chain, and the hydrophobic polymer segment 13 typified by a polyamino acid chain. The drug 14 is bound to the hydrophobic polymer segment 13 through an ester bond or an amide bond. As described above, the backbone polymer unit α 10 has the target binding site 11 and is free from the drug 14, and the backbone polymer unit β 20 has the drug 14 and is free from the target binding site 11. In addition, the backbone polymer unit α 10 and the backbone polymer unit β 20 are disposed in a radial arrangement in a state where the target binding site 11 is directed outward and the drug 14 is directed inward. As shown in FIG. 6A, the polymer micelle 100 may contain a backbone polymer unit γ 30 that is free from the target binding site 11 and the drug 14 and is made up of the hydrophilic polymer segment 12 and the hydrophobic polymer segment 13.

In the present specification, the state where the backbone polymer unit α 10 and the backbone polymer unit β 20 are disposed in a radial arrangement may be a state where the units are aggregated with the target binding site 11 being directed outward and the drug 14 being directed inward, and may be a micelle having a slightly collapsed radial arrangement structure in which starting points of arrangement of the respective units are not coincident with each other. The polymer micelle 100 may be a dried polymer aggregate made up of the backbone polymer unit α 10 and the backbone polymer unit β 20.

Figure 6B:
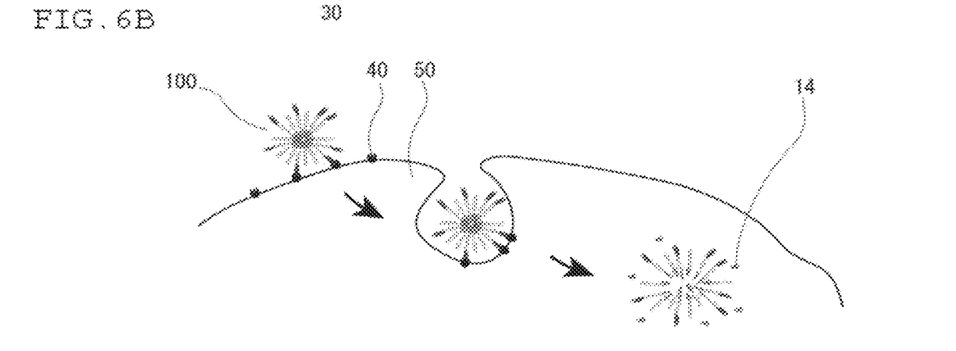

As shown in FIG. 6B, it is conceivable that, when the polymer micelle 100 is bound to the target 40 while maintaining a radial arrangement, the micelle is taken up into a cell 50 supplying a target 40 through endocytosis (represented in the center in FIG. 6B), and then the encapsulated drug 14 is released into the cell 50 by collapse of the radial arrangement in the cell 50. More specifically, it is conceivable that the backbone polymer unit β 20 transits into a lysosome in the cell 50, and the drug 14 is released by cleavage of an ester bond with an enzyme typified by an esterase.

Figure 6C:
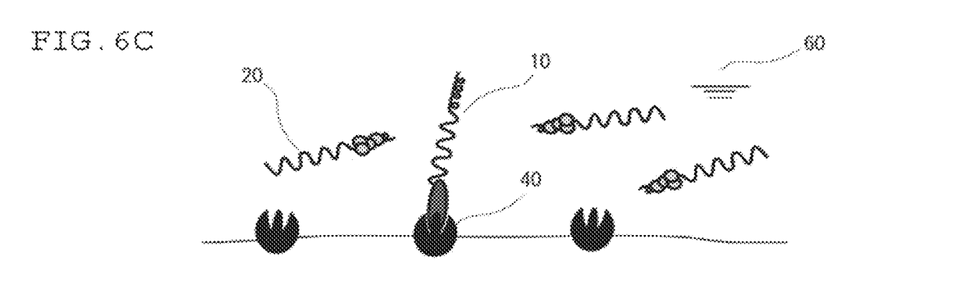

It is known that, in principle, a polymer having a molecular weight of several tens of thousands or less is rapidly excreted into the urine via the kidney. Therefore, even if the radial arrangement of the polymer micelle 100 collapses before the micelle is taken up into a dosing target as shown in FIG. 6C and the drug 14 is exposed to blood 60, the backbone polymer unit β 20 having a molecular weight of several tens of thousands or less is not fixed to the target 40, so that the drug 14 is not continuously exposed to the blood 60 and is rapidly eliminated from the body through metabolism. Thus, the polymer micelle 100 has been provided with a safety mechanism for preventing a normal cell from being damaged by a drug even when a micelle structure collapses before the micelle is taken up into a dosing target.

It is preferred that the backbone polymer unit α be represented by the general formula I: $Z-A_1-B_1$ and be made up of a compound having a target binding site and a block copolymer, and the backbone polymer unit β be represented by the general formula II: $A_2-B_2(-D)$ and be made up of a drug and a block copolymer. In the formulae: Z represents a residue of a compound having a target binding site; $A_1$ and $A_2$ each independently represent a polyethylene glycol chain segment; $B_1$ and $B_2$ each independently represent a polyamino acid chain segment; and D represents a drug.

The backbone polymer unit α may be formed by a condensation or addition reaction of a block copolymer having a linking group such as a hydroxyl group, a carboxyl group, an aldehyde group, an amino group, a mercapto group, and a maleimide group at the α-terminus of the polyethylene glycol chain segment, and the compound having a target binding site.

The α-terminus of the polyethylene glycol chain segment in the backbone polymer unit β may have the above-mentioned linking group such as a hydroxyl group, and preferably has a linear or branched alkyl group or alkoxy group having 1 to 12 carbon atoms ($C_1$ to $C_{12}$) or a hydroxyl group.

Examples of the polyamino acid chain segment include polyglutamic acid or its ester or amide derivative, and polyaspartic acid or its ester or amide derivative. Such ester or amide derivative may be formed by allowing a corresponding hydroxy compound or amino compound having a hydrophobic organic group to react with a reactive derivative (for example, an ester) of polyglutamic acid or polyaspartic acid. Examples of the hydrophobic organic group include an alkyl having 1 to 6 carbon atoms ($C_1$ to $C_6$)-phenyl, cholesterol, and a linear or branched alkyl having 8 to 18 carbon atoms ($C_8$ to $C_{18}$).

The block copolymer in the backbone polymer unit α and the backbone polymer unit β may be formed by, for example, the method described in JP 02-300133 A, i.e., performing a reaction by using $Y-PEG-CH_2CH_2CH_2-NH_2$ (Y represents a functional group or a substituent which may be protected) as an initiator, and in a dehydrated organic solvent, adding N-carboxy-γ-benzyl-L-glutamate or N-carboxy-β-benzyl-L-aspartate so as to achieve a desired degree of polymerization. When a more bulky hydrophobic group than a benzyl group is incorporated, the benzyl group may be substituted by a $C_4$ alkyl-phenyl group, cholesterol, or a $C_8$ to $C_{18}$ alkyl group. For such hydrophobic group, a hydrophobic compound having a hydroxyl group or an amino group may be incorporated into a polyglutamic acid side chain by using a condensation agent such as dicyclohexylcarbodiimide and diisopropylcarbodiimide in a dehydrated organic solvent.

It is preferred that the backbone polymer unit α have a structure represented by the below-indicated general formula I-a or I-b, and the backbone polymer unit β have a structure represented by the below-indicated general formula II-a or II-b:

where: $R_1$ represents a residue of a compound having a target binding site; $R_2$ represents an alkyl group having 1 to 12 carbon atoms which may have a hydroxyl group at the terminus; $L_1$ represents $O(CH_2)_pNH$; $L_2$ represents $O(CH_2)_p—CO—$; p represents an integer ranging from 1 to 5; R represents a hydrogen atom or a hydrophobic organic group; q represents 1 or 2; $n_1$ and $n_2$ each independently represent an integer ranging from 40 to 450; $m_1$ and $m_2$ each independently represent an integer ranging from 20 to 80; $R_3$ represents a residue of a drug, provided that at least 10% to 70% of the total number $m_2$ may have a linking group; and if present, the rest group is a hydrogen atom or a hydrophobic organic group.

Both of $n_1$ and $n_2$ represent preferably an integer ranging from 40 to 450, more preferably an integer ranging from 70 to 350, and particularly preferably an integer ranging from 110 to 280. Both of $m_1$ and $m_2$ represent preferably an integer ranging from 20 to 80 and more preferably an integer ranging from 25 to 50. The numerical values of $n_1$, $n_2$, $m_1$, and $m_2$ are average values.

In the polymer micelle 100, the backbone polymer unit α 10 and the backbone polymer unit β 20 are present in a range of 1:19 to 19:1 at a molar ratio.

As described above, examples of the compound having the target binding site 11 include a protein, a peptide, or a sugar chain forming a bonding pair with a substance derived from a living body and a virus. Examples of such protein include an antibody that binds to a substance derived from a living body and a virus and a fragment thereof, transferrin, and epidermal growth factor (EGF). Examples of the antibody include antibodies that recognize antigens such as EGFR, Her2, CD20, VEGFR, and CD52 as receptor and cell surface antigens highly expressed on the surface of a dosing target typified by a cancer cell. The antibody may be a monoclonal antibody or a polyclonal antibody. The fragment of the antibody may be any fragment having a length sufficient for specifically recognizing an antigen, and examples thereof include (Fab')2 and Fab. Examples of the peptide include insulin, LHRH, IGF, and derivatives thereof. Examples of the sugars include sugars having glucose, mannose, galactose, and fucose residues.

When the target 40 with which the residue of the compound having the target binding site 11 forms a bonding pair is a substance derived from a virus, a cell supplying the substance is in a dead state by cell membrane destruction due to an infecting virus, and hence, the polymer micelle 100 cannot be taken up into the cell through endocytosis. Thus, in the present specification, when the target 40 is a substance derived from a virus, a cell present around the target 40 is regarded as the cell supplying the target 40. When the substance derived from a virus is present outside the cell, such marginal cell is also infected with a virus at high possibility, and thus, it is significant to supply a drug to the marginal cell.

Examples of the drug 14 include a nucleic acid derivative, docetaxel, camptothecins, epothilone A, epothilone B, epothilone C, epothilone D, and derivatives of those epothilones, temsirolimus, everolimus, trabectedin, vorinostat, octreotide acetate, mitoxantrone, vincristine, cefalexin, cefaclor, ampicillin, bacampicillin, amoxycillin, kanamycin, arbekacin, dibekacin, sisomicin, tobramycin, erythromycin, clarithromycin, rokitamycin, chloramphenicol, vancomycin, fluconazole, vidarabine, acyclovir, didanosine, zidovudine, zalcitabine, lamivudine, zanamivir, oseltamivir, lopinavir, and ritonavir. Examples of the nucleic acid derivative include gemcitabine, nelarabine, clofarabine, decitabine, streptozocin, doxifluridine, and fludarabine. The nucleic acid derivative may be a salt. However, it is preferred that the nucleic acid derivative be not a salt when being allowed to bind to the backbone polymer unit β through an ester bond. For derivatives of epothilones, there are exemplified patupilone, ixabepilone, BMS-310705, KOS-862, and ZK-EPO.

When a plurality of hydroxyl groups are present in a drug, the backbone polymer unit β may take a structure in which one or more of the hydroxyl groups is/are bound to a carboxyl group in a polyglutamic acid side chain through an ester bond. In the present specification, the backbone polymer unit β also involves a structure in which one drug is bound to a plurality of carboxyl groups in a polyglutamic acid side chain through an ester bond, and a structure in which two or more of block copolymer moieties are cross-linked via one drug.

The polymer micelle of the present invention may be formed by, for example, mixing the backbone polymer unit α with the backbone polymer unit β in an aqueous solution and allowing the mixture to self-assemble into a micelle form. Further, the polymer micelle of the present invention may be formed by, for example, mixing the backbone polymer unit β with the backbone polymer unit γ in an aqueous solution, allowing the mixture to self-assemble into a micelle form, and then allowing a compound having a target binding site to bind to the α-terminus of a hydrophilic segment in the backbone polymer unit γ. The aqueous solution may be formed by, for example, adding a water-compatible organic solvent such as ethanol and dimethylsulfoxide and a conventional buffer to purified water. The preparation of plural kinds of backbone polymer units α having target binding abilities different from each other, and plural kinds of backbone polymer units β to which drugs different from each other have been bound provides convenience because various active targeting polymer micelles encapsulating drugs may be easily formed by appropriately combining the respective units.

A conventional active targeting DDS typified by the polymer conjugate as described in WO 2002/087497 is formed by allowing a compound having a target binding site to bind to a block copolymer to which a drug has been bound via an ester bond. However, in the process of allowing a drug to bind to a block copolymer, a functional group or a substituent to which a residue of the compound having a target binding site binds in the block copolymer may lose its binding ability to the compound. Further, the drug may be degraded in the process of allowing the compound to bind. Therefore, it is difficult to prepare the conventional active targeting DDS in a simple manner. On the other hand, as described above, by using the polymer micelle of the present invention, various active targeting polymer micelles encapsulating drugs may be easily formed while avoiding deactivation of the medicament.

According to the present invention, there can also be provided a pharmaceutical composition containing the above-mentioned polymer micelle and a pharmaceutically acceptable carrier. The pharmaceutically acceptable carrier may be a diluent and an excipient commonly used in the technical field depending on a dosage form of interest, and preferably is purified water, deionized water, an isotonic agent, and a pH adjustor suitable for preparation of a liquid formulation and a lyophilized formulation as parenteral formulations.

The administration route of the pharmaceutical composition of the present invention is preferably a parenteral administration such as a subcutaneous administration, an intravenous administration, an intraarterial injection, and a local administration, and particularly preferably an intravenous injection. The dose of the pharmaceutical composition should be appropriately adjusted depending on the kind and usage of a drug, the age and gender of a patient, and the health status of a patient, and is set to a range of 0.1 to 10,000 mg/m$^2$ and preferably a range of 1 to 1,000 mg/m$^2$ per day in terms of a drug.

EXAMPLES

Hereinafter, the present invention is described in more detail by way of examples.

Example 1

A transferrin bound camptothecin micelle, which was a polymer micelle having transferrin as the compound having a target binding site, and encapsulating camptothecin (CPT) as the drug, was formed as follows.

First, as the backbone polymer unit β, a camptothecin conjugate (PEG-pGlu-CPT) was formed as follows. 1 g of PEG-pGlu-Ac was dissolved in 80 mL of anhydrous dimethylformamide (anhydrous DMF). After that, 387 mg of camptothecin (Wako Pure Chemical Industries, Ltd.) were added thereto. In PEG-pGlu-Ac, PEG has a chain length of 12 kDa, the average number of glutamic acid residues is 40, and a glutamic acid side chain is a carboxylic acid. Subsequently, 823 mg of N,N'-diisopropylcarbodiimide (KOKUSAN CHEMICAL Co., Ltd.) and 136 mg of dimethylaminopyridine (Wako Pure Chemical Industries, Ltd.) were added in the stated order, and the mixture was stirred at 4° C. for 3 days. After the temperature had been raised to room temperature, the mixture was further stirred overnight. The reaction liquid thus obtained was transferred into a dialysis tube (Spectrum Laboratories, Spectra/Por® molecular weight cutoff 3500) and dialyzed with purified water at 4° C. After the removal of a white precipitate, the obtained yellow solution was filtered through a filter with a pore diameter of 0.8 μm (Millex®-AA manufactured by Millipore Corporation). The filtrate was lyophilized to afford 1.1 g of PEG-pGlu-CPT as a pale yellow powder. PEG-pGlu-CPT is in a state (MeO-PEG-pGlu-CPT) where camptothecin is bound to PEG-pGlu via an ester bond. PEG-pGlu-CPT has a structure represented by the above general formula II-a. PEG has a chain length of 12 kDa.

A polymer (Maleimide-PEG-PBLA) having a maleimide group at the PEG terminus was prepared. In the polymer, PEG has a chain length of 12 kDa. 10 mg of PEG-pGlu-CPT and 10 mg of Maleimide-PEG-PBLA were precisely weighed in a sample vial and supplemented with 1 mL of purified water. The mixture was stirred at 4° C. for a whole day and night, then subjected to ultrasonication using a biodisruptor (High Power Unit manufactured by NISSEI Corporation) under cooling with ice for 10 minutes, and filtered through a 0.22-1 μm filter (Millex®GP PES manufactured by Millipore Corporation) to recover a filtrate. The filtrate was subjected to gel filtration [PD-10 manufactured by GE Healthcare Bio-Sciences Ltd., eluent: 20 mM sodium phosphate buffer (pH 7.0)] to recover a micelle fraction (1.5 mL). The micelle fraction contains a micelle having PEG-pGlu-CPT and Maleimide-PEG-PBLA disposed in a radial arrangement.

To 40 mg of human-derived transferrin (Sigma-Aldrich Corporation) (hereinafter, transferrin may be referred to as Tf), a 0.2 M borate buffer (pH 8.0), 100 mM ethylenediaminetetraacetic acid (EDTA), and purified water were added to dissolve Tf. Subsequently, 138 μL of a 10 mg/mL Traut's reagent (Pierce Chemical Co.) were further added so that the final concentration of the borate buffer would be 50 mM and the final concentration of EDTA would be 2 mM, to thereby prepare a total of 1 mL of a mixed liquid. After that, the mixed liquid was left to stand still at 30° C. for 45 minutes. The reaction liquid thus obtained was subjected to gel filtration [PD-10 manufactured by GE Healthcare Bio-Sciences Ltd., eluent: 20 mM sodium phosphate buffer (pH 7.0), 2 mM EDTA] to recover a polymer fraction (1.5 mL).

0.75 mL of the recovered liquid and 0.75 mL of the above-mentioned micelle fraction were mixed with each other and left to stand still at 30° C. for 2 hours, to thereby allow a maleimide group in Maleimide-PEG-PBLA to react with Tf. Thus, a micelle Containing a transferrin bound polymer as the backbone polymer unit α was formed. The transferrin bound polymer has a structure represented by the above general formula I-a. PEG has a chain length of 12 kDa. In the reaction liquid, the sodium phosphate buffer has a final concentration of 20 mM, and EDTA has a final concentration of 1 mM. Subsequently, a 200 mM ammonium formate buffer was added to the reaction liquid to adjust the pH to 5. After that, the reaction liquid was purified by gel filtration [Sepharose CL-4B (1Φ×30 cm), eluent: 20 mM sodium acetate buffer (pH 5.0)] to remove unreacted Tf.

The recovered micelle fraction was concentrated to about 2 mL by ultrafiltration (Amicon Ultra-15 manufactured by Millipore Corporation), then supplemented with an NaHCO$_3$—Na$_2$CO$_3$ buffer (pH 9.6) so as to adjust the pH to 7, further supplemented with 20 μL of a 100 mM cysteine solution, and left to stand still at room temperature for 10 minutes. The reaction liquid thus obtained was subjected to gel filtration [PD-10 manufactured by GE Healthcare Bio-Sciences Ltd., eluent: 20 mM sodium phosphate buffer (pH 7.4)] to recover a polymer fraction (3 mL). To the polymer fraction, added were 30 μL each of 1 M FeCl$_3$ and 100 mM Na$_2$CO$_3$ (adjusted with 100 mM citric acid so as to have a pH of 7.0). The mixed liquid thus obtained was left to stand still at 4° C. overnight, and then subjected to ultrafiltration (Amicon Ultra-15 manufactured by Millipore Corporation). The mixed liquid was finally concentrated to about 2 mL by repeatedly performing the dilution with a 20 mM sodium phosphate buffer (pH 7.4) and the removal of an iron ion. The concentrated liquid was filtered through a 0.22-μm filter (Millex®GV manufactured by Millipore Corporation) to recover a filtrate. Thus, a solution containing a transferrin bound camptothecin micelle was obtained.

Example 2

A transferrin bound docetaxel micelle, which was a polymer micelle having transferrin as the compound having a target binding site, and encapsulating docetaxel as the drug, was formed in the same manner as in Example 1 except that the backbone polymer unit β was changed to a docetaxel conjugate (PEG-pGlu-DTX) by using docetaxel (DTX) as the drug. The PEG forming block copolymer moieties in the backbone polymer unit α and the backbone polymer unit β had a chain length of 10 kDa in both units. PEG-pGlu-DTX is in a state (MeO-PEG-pGlu-DTX) where docetaxel is bound to PEG-pGlu via an ester bond, and has a structure represented by the above general formula II-a.

PEG-pGlu-DTX as the backbone polymer unit β was formed as follows. 500 mg of a polyethylene glycol-polyglutamic acid block copolymer (PEG-pGlu-Ac) in which polyglutamic acid had been acetylated at one terminus were dissolved in 10 mL of anhydrous DMF (Kanto Chemical Co., Inc.). After that, 1.06 g of docetaxel (ScinoPharm Taiwan, Ltd) were added thereto. In PEG-pGlu-Ac, PEG has an average molecular weight of 10,000, the average number of glutamic acid residues is 40, and a glutamic acid side chain is a carboxylic acid. Subsequently, 160 mg of 4-dimethylaminopyridine (Wako Pure Chemical Industries, Ltd.) and 210 μL of N,N'-diisopropylcarbodiimide (KOKUSAN CHEMICAL Co., Ltd.) were added in the stated order, and the mixture was stirred at room temperature overnight. The reaction liquid thus obtained was dropped into 500 mL of a mixed solution of hexane and ethyl acetate (volume ratio: 1:1) to crystallize a polymer. After that, the polymer was collected by filtration under reduced pressure. The polymer collected by filtration was suspended in 100 mL of purified water to prepare a polymer micelle. The polymer micelle was subjected to ultrafiltration (Labscale TFF System manufactured by Millipore Corporation, molecular weight cutoff value: 100,000, diluted 5-fold and then concentrated to 100 mL). The ultrafiltration operation was repeatedly performed 5 times, followed by lyophilization. The polymer obtained by lyophilization, which had been dissolved in 10 mL of anhydrous DMF, was dropped into 500 mL of a mixed solution of hexane and ethyl acetate (volume ratio: 1:1) to crystallize a polymer. After that, the polymer was collected by filtration under reduced pressure. The polymer collected by filtration in a powder form was washed by adding the polymer to 100 mL of a mixed solution of hexane and ethyl acetate (volume ratio: 1:1) and then collected by filtration under reduced pressure. The polymer collected by filtration was dried under reduced pressure at room temperature overnight to afford 530 mg of PEG-pGlu-DTX as a pale yellow powder.

1 mg of PEG-pGlu-DTX was dissolved in 10 mL of a mixed solution of purified water and ethanol (volume ratio: 1:1). The content of docetaxel was measured by the absorbance of light at a wavelength of 233 nm and found to be 14.3 molecules per polymer. PEG-pGlu-DTX is in a state (MeO-PEG-pGlu-DTX) where docetaxel is bound to PEG-pGlu-Ac via an ester bond. PEG-pGlu-DTX has a structure represented by the above general formula II-a. PEG has a chain length of 10 kDa.

Example 3

An EGF bound docetaxel micelle, which was a polymer micelle having epidermal growth factor (EGF) as the compound having a target binding site, and encapsulating docetaxel (DTX) as the drug, was formed as follows.

A DTX conjugate (PEG-pGlu-DTX) as the backbone polymer unit β was formed in the same manner as in Example 2.

A polymer (Maleimide-PEG-PBLA) having a PEG chain length of 10 kDa and having a maleimide group at the PEG terminus was prepared. 5 mg of the polymer and 5 mg of PEG-pGlu-DTX were precisely weighed in a sample vial, supplemented with 1 mL of purified water, and then treated in the same manner as in Example 1, to thereby recover a micelle fraction (1.5 mL). The micelle fraction contains a micelle having PEG-pGlu-DTX and Maleimide-PEG-PBLA disposed in a radial arrangement.

To a vial loaded with 1 mg of recombinant human EGF (R&D Systems, Inc.), 1 mL of purified water was added to prepare a 1 mg/mL EGF solution. To 0.5 mL of the EGF solution, a 0.2 M borate buffer (pH 8.0), 100 mM ethylenediaminetetraacetic acid (EDTA), and purified water were added, and 138 μL of a 10 mg/mL Traut's reagent (Pierce Chemical Co.) were further added so that the final concentration of the borate buffer would be 50 mM and the final concentration of EDTA would be 2 mM, to thereby prepare a total of 1 mL of a mixed liquid. After that, the mixed liquid was left to stand still at 30° C. for 45 minutes. Subsequently, the reaction liquid thus obtained was subjected to gel filtration [PD-10 manufactured by GE Healthcare Bio-Sciences Ltd., eluent: 20 mM sodium phosphate buffer (pH 7.0), 2 mM EDTA] to recover a polymer fraction (1.5 mL).

1.5 mL of the recovered liquid and 0.5 mL of the above-mentioned micelle fraction were mixed with each other and left to stand still at 30° C. for 2 hours, to thereby allow a maleimide group in Maleimide-PEG-PBLA to react with EGF. Thus, a micelle containing an EGF bound polymer as the backbone polymer unit α was formed. The EGF bound polymer has a structure represented by the above general formula I-a. The reaction liquid thus obtained was purified by gel filtration [Sepharose CL-4B (1Φ×30 cm), eluent: 20 mM sodium acetate buffer (pH 7.4)] to remove unreacted EGF.

The recovered micelle fraction was concentrated to about 2 mL by ultrafiltration (Amicon Ultra-15 manufactured by Millipore Corporation) to afford a solution containing an EGF bound docetaxel micelle.

Example 4

An anti-RANKL antibody bound everolimus micelle, which was a polymer micelle having an anti-RANKL antibody as the compound having a target binding site, and encapsulating everolimus (EVE) as the drug, was formed as follows.

First, an everolimus conjugate (PEG-pGlu-EVE) as the backbone polymer unit β was formed as follows. 140 mg of a polyethylene glycol-polyglutamic acid block copolymer (PEG-pGlu-Ac) in which polyglutamic acid had been acetylated at one terminus were dissolved in 10 mL of anhydrous DMF (Kanto Chemical Co., Inc.) and then further supplemented with 142 mg of everolimus (MOLCAN. Co.). In PEG-pGlu-Ac, PEG has an average molecular weight of 10,000, the average number of glutamic acid residues is 40, and a glutamic acid side chain is a carboxylic acid. Subsequently, 16.9 mg of 4-dimethylaminopyridine (Wako Pure Chemical Industries, Ltd.) and 22.0 μL of N,N'-diisopropylcarbodiimide (KOKUSAN CHEMICAL Co., Ltd.) were added in the stated order, and the mixture was stirred at room temperature overnight. The reaction liquid thus obtained was dropped into 100 mL of a mixed solution of hexane and ethyl acetate (volume ratio: 3:1) to crystallize a polymer. After that, the polymer was collected by filtration under reduced pressure. The polymer collected by filtration, which had been dissolved in anhydrous DMF, was dialyzed with 1 L of distilled water for 2 days [molecular weight cutoff (MWCO) =3500, distilled water was exchanged 4 times] and then lyophilized. The polymer obtained by lyophilization, which had been dissolved in 10 mL of anhydrous DMF, was dropped into 100 mL of a mixed solution of hexane and ethyl acetate (volume ratio: 3:1) to crystallize a polymer. After that, the polymer was collected by filtration under reduced pressure. The polymer collected by filtration in a powder form was washed by adding the polymer to 100 mL of a mixed solution of hexane and ethyl acetate (volume ratio: 3:1) and collected by filtration under reduced pressure. The polymer collected by filtration was dried under reduced pressure at room temperature overnight to afford 180 mg of PEG-pGlu-EVE as a pale yellow powder.

1 mg of PEG-pGlu-EVE was dissolved in 25 mL of a mixed solution (volume ratio: 1:1) of purified water and methanol. The content of everolimus was measured by the absorbance of light at a wavelength of 278 nm and found to be 12.6 molecules per polymer. PEG-pGlu-EVE is in a state (MeO-PEG-pGlu-EVE) where everolimus is bound to PEG-pGlu via an ester bond. PEG-pGlu-EVE has a structure represented by the above general formula II-a. PEG has a chain length of 10 kDa.

5 mg of PEG-pGlu-EVE were precisely weighed in a sample vial and supplemented with 1 mL of purified water. The mixture was stirred at 4° C. for a whole day and night, then subjected to ultrasonication using a biodisruptor (High Power Unit manufactured by NISSEI Corporation) under cooling with ice for 10 minutes, and filtered through a 0.22-

μm filter (Millex®GP PES manufactured by Millipore Corporation) to recover a filtrate. The filtrate contains PEG-pGlu-EVE as the backbone polymer unit β.

An anti-RANKL antibody bound polymer as the backbone polymer unit α was formed as follows. A polymer (Maleimide-PEG-PBLA) having a maleimide group at the PEG terminus was prepared. In the polymer, PEG has a chain length of 10 kDa. 5 mg of Maleimide-PEG-PBLA were precisely weighed in a sample vial, and 1 mL of a 20 mM sodium phosphate buffer (pH 7.0) was added thereto. The mixture was stirred at 4° C. for a whole day and night, then subjected to ultrasonication by using a biodisruptor (High Power Unit manufactured by NISSEI Corporation) under cooling with ice for 10 minutes, and filtered through a 0.22-μm filter (Millex®GP PES manufactured by Millipore Corporation) to recover a filtrate containing Maleimide-PEG-PBLA.

To a vial loaded with 500 μg of an anti-RANKL antibody (R&D Systems, Inc.), 0.5 mL of PBS was added to prepare a 1 mg/mL anti-RANKL antibody solution. To 0.4 mL of the anti-RANKL antibody solution, a 0.2 M borate buffer (pH 8.0), 100 mM EDTA, and purified water were added, and 2 μL of a 10 mg/mL Traut's reagent (Pierce Chemical Co.) were further added so that the final concentration of the borate buffer would be 50 mM and the final concentration of EDTA would be 2 mM, to thereby prepare a total of 0.6 mL of a mixed liquid. After that, the mixed liquid was left to stand still at 30° C. for 45 minutes. Subsequently, the reaction liquid thus obtained was subjected to gel filtration [PD-10 manufactured by GE Healthcare Bio-Sciences Ltd., eluent: 20 mM sodium phosphate buffer (pH 7.0), 2 mM EDTA] to recover a polymer fraction (1.5 mL).

1.5 mL of the recovered liquid and 38 μL of the above-mentioned filtrate containing Maleimide-PEG-PBLA were mixed with each other, left to stand still at 30° C. for 2 hours, and further left to stand still at 4° C. overnight, to thereby allow a maleimide group in Maleimide-PEG-PBLA to react with an anti-RANKL antibody. Thus, an anti-RANKL antibody bound polymer as the backbone polymer unit α was formed. The anti-RANKL antibody bound polymer has a structure represented by the above general formula I-a. The reaction liquid thus obtained was purified by gel filtration [Sepharose CL-4B (1Φ×30 cm), eluent: 20 mM sodium phosphate buffer (pH 7.4)] to remove an unreacted SH-modified antibody.

The recovered micelle fraction was concentrated to about 1 mL by ultrafiltration (Amicon Ultra-15 manufactured by Millipore Corporation, molecular weight cutoff value: 100,000) to afford a solution containing an anti-RANKL antibody bound polymer.

36 μL of the filtrate containing PEG-pGlu-EVE and 500 μL of the solution containing an anti-RANKL antibody bound polymer were mixed with each other and left to stand still at 4° C. for 3 days, to thereby afford a solution containing an anti-RANKL antibody bound everolimus micelle. The anti-RANKL antibody bound everolimus micelle had an average particle diameter of 119 nm, which was measured with a Zetasizer (Malvern Instruments Ltd.).

Example 5

A transferrin bound everolimus micelle, which was a polymer micelle having transferrin as the compound having a target binding site, and encapsulating everolimus (EVE) as the drug, was formed as follows.

In the same manner as in Example 4, a filtrate containing PEG-pGlu-EVE as the backbone polymer unit β was obtained.

A transferrin bound polymer as the backbone polymer unit α was formed as follows. First, in the same manner as in Example 4, a filtrate containing Maleimide-PEG-PBLA was obtained. 10 mg of human transferrin (Sigma-Aldrich Corporation) were dissolved in 1 mL of purified water to prepare a transferrin solution. To 696 μL of the transferrin solution, a 0.2 M borate buffer (pH 8.0), 100 mM EDTA, and purified water were added, and 34 μL of a 10 mg/mL Traut's reagent (Pierce Chemical Co.) were further added so that the final concentration of the borate buffer would be 50 mM and the final concentration of EDTA would be 2 mM, to thereby prepare a total of 1 mL of a mixed liquid. After that, the mixed liquid was left to stand still at 30° C. for 45 minutes. Subsequently, the reaction liquid thus obtained was subjected to gel filtration [PD-10 manufactured by GE Healthcare Bio-Sciences Ltd., eluent: 20 mM sodium phosphate buffer (pH 7.0), 2 mM EDTA] to recover a polymer fraction (1.5 mL).

1.5 mL of the recovered liquid and 0.9 mL of the above-mentioned filtrate containing Maleimide-PEG-PBLA (polymer concentration: 5 mg/mL) were mixed with each other, left to stand still at 30° C. for 2 hours (final concentration of sodium phosphate buffer (pH 7.0): 20 mM, final concentration of EDTA: 1 mM), and further left to stand still at 4° C. overnight, to thereby allow a maleimide group in Maleimide-PEG-PBLA to react with transferrin. Thus, a transferrin bound polymer as the backbone polymer unit α was formed. The transferrin bound polymer has a structure represented by the above general formula I-a.

The reaction liquid thus obtained was purified by gel filtration [Sepharose CL-4B (1Φ×30 cm), eluent: 20 mM sodium phosphate buffer (pH 7.4)] to remove unreacted SH-modified transferrin. The recovered micelle fraction was concentrated to about 2 mL by ultrafiltration (Amicon Ultra-15 manufactured by Millipore Corporation, molecular weight cutoff value: 100,000), then supplemented with an $NaHCO_3$—$Na_2CO_3$ buffer (pH 9.6) to adjust the pH to 7, and further supplemented with 20 μL of a 100 mM cysteine solution, and the mixture was left to stand still at room temperature for 10 minutes. The reaction liquid thus obtained was subjected to gel filtration [PD-10 manufactured by GE Healthcare Bio-Sciences Ltd., eluent: 20 mM sodium phosphate buffer (pH 7.4)] to recover a polymer fraction (3 mL). To the polymer fraction, added were 30 μL each of 1 M $FeCl_3$ and 100 mM $Na_2CO_3$ (adjusted to a pH of 7.0 with 100 mM citric acid). The mixed liquid thus obtained was left to stand still at 4° C. overnight and then subjected to ultrafiltration (Amicon Ultra-15 manufactured by Millipore Corporation, molecular weight cutoff value: 100,000). The mixed liquid was finally concentrated to about 3 mL by repeatedly performing the dilution with a 20 mM sodium phosphate buffer (pH 7.4) and the removal of an iron ion, to thereby afford a solution containing a transferrin bound polymer.

200 μL of the filtrate containing PEG-pGlu-EVE and 500 μL of the solution containing a transferrin bound polymer were mixed with each other and left to stand still at 4° C. for 3 days, to thereby afford a solution containing a transferrin bound everolimus micelle. The transferrin bound everolimus micelle had an average particle diameter of 106 nm, which was measured with a Zetasizer (Malvern Instruments Ltd.).

Comparative Example 1

A polymer micelle that was free from a residue of a compound having a target binding site and encapsulated docetaxel as the drug (hereinafter, referred to as Tf unbound DTX micelle for ease of explanation) was formed as follows. 10 mg of PEG-pGlu-DTX formed in Example 2 were precisely weighed in a sample vial, supplemented with 1 mL of a 20 mM sodium phosphate buffer (pH 7.0), and suspended. The suspension was stirred at 4° C. for a whole day and night and then subjected to ultrasonication with a biodisruptor (High Power Unit manufactured by NISSEI Corporation) under cooling with ice for 10 minutes, and filtered through a filter with a pore diameter of 0.22 μm [Millex®GP PES manufactured by Millipore Corporation] to recover a filtrate. The filtrate was subjected to gel filtration (PD-10 manufactured by GE Healthcare Bio-Sciences Ltd., eluent: 10% sucrose solution) to afford a polymer fraction containing a Tf unbound DTX micelle.

Comparative Example 2

A polymer micelle that was free from a residue of a compound having a target binding site and encapsulated camptothecin as the drug (hereinafter, referred to as Tf unbound CPT micelle for ease of explanation) was formed as follows. 10 mg of PEG-pGlu-CPT formed in Example 1 were precisely weighed in a sample vial, supplemented with 1 mL of purified water, and suspended. The suspension was stirred at 4° C. for a whole day and night, then subjected to ultrasonication with a biodisruptor (High Power Unit manufactured by NISSEI Corporation) under cooling with ice for 10 minutes, and filtered through a filter with a pore diameter of 0.22 μm [Millex®GP PES manufactured by Millipore Corporation] to recover a filtrate. The filtrate was subjected to gel filtration (PD-10 manufactured by GE Healthcare Bio-Sciences Ltd., eluent: 20 mM sodium phosphate buffer (pH 7.0)) to afford a polymer fraction containing a Tf unbound CPT micelle.

Comparative Example 3

A polymer micelle that had Tf as the compound having a target binding site and was free from a drug (hereinafter, referred to as Tf bound empty micelle for ease of explanation) was formed as follows.
A polymer (Maleimide-PEG-PBLG) having a maleimide group at the PEG terminus was prepared. In the polymer, PEG has a chain length of 10 kDa. 5 mg of Maleimide-PEG-PBLG were precisely weighed in a sample vial and supplemented with 1 mL of a 20 mM sodium phosphate buffer (pH 7.0). The mixture was stirred at 4° C. for a whole day and night, then subjected to ultrasonication using a biodisruptor (High Power Unit manufactured by NISSEI Corporation) under cooling with ice for 10 minutes, and filtered through a 0.22-μm filter (Millex®GP PES manufactured by Millipore Corporation), to thereby recover a filtrate containing Maleimide-PEG-PBLG.
To 10 mg of human-derived Tf (Wako Pure Chemical Industries, Ltd.), a 0.2 M borate buffer (pH 8.0), 100 mM ethylenediaminetetraacetic acid (EDTA), and purified water were added to dissolve Tf. Subsequently, 34 μL of a 10 mg/mL Traut's reagent (Pierce Chemical Co.) were further added so that the final concentration of the borate buffer would be 50 mM and the final concentration of EDTA would be 2 mM, to thereby prepare a total of 1 mL of a mixed liquid. After that, the mixed liquid was left to stand still at 30° C. for 45 minutes. The reaction liquid thus obtained was subjected to gel filtration [PD-10 manufactured by GE Healthcare Bio-Sciences Ltd., eluent: 20 mM sodium phosphate buffer (pH 7.0), 2 mM EDTA] to recover a polymer fraction (1.5 mL).
1.5 mL of the recovered liquid and 0.9 mL of the above-mentioned filtrate containing Maleimide-PEG-PBLG were mixed with each other, left to stand still at 30° C. for 2 hours, and further left to stand still at 4° C. overnight, to thereby allow a maleimide group in Maleimide-PEG-PBLG to react with Tf. The reaction liquid thus obtained was purified by gel filtration [Sepharose CL-4B (2Φ×30 cm), eluent: 20 mM sodium phosphate buffer (pH 7.0)] to remove unreacted SH-modified Tf.
The polymer fraction recovered by gel filtration was subjected to ultrafiltration (Amicon Ultra-15 manufactured by Millipore Corporation, molecular weight cutoff value: 100,000) to recover a polymer fraction (4 mL). With 0.5 mL of the polymer fraction, 50 μL of 100 mM $FeCl_3$ (100 mM citric acid adjusted with 1 M $Na_2CO_3$ so as to have a pH of 7.0) were mixed. The mixed liquid thus obtained was left to stand still at 4° C. for 2 hours. After that, an excess iron ion was removed by gel filtration [PD-10 manufactured by GE Healthcare Bio-Sciences Ltd., eluent: 20 mM sodium phosphate buffer (pH 7.0)] to afford a solution containing a Tf bound empty micelle.

Cytotoxicity Test 1

The cytotoxicity of the Tf bound DTX micelle in Example 2 was compared with the cytotoxicity of the Tf unbound DTX micelle in Comparative Example 1. The cytotoxicity of each micelle was evaluated based on a WST method by using a human breast cancer MDA-MB-231 cell purchased from European Collection of Cell Culture (ECACC) via DS Pharma Biomedical Co., Ltd. as described below.
The human breast cancer MDA-MB-231 cell, which had been suspended in 90 μlL of a medium, was seeded to a 96-well plate so that the cell would be contained at a concentration of about 5000 cells per well, and cultivated under an atmosphere of 37° C. and 5% $CO_2$ overnight. The medium was formed of RPMI1640 (Gibco™, Invitrogen) and 10% Fetal Bovine Serum (FBS, biowest). Subsequently, each of sample liquids at various DTX concentrations obtained by diluting the micelle solution in Example 2 and the micelle solution in Comparative Example 1 with the medium was added to each well (10 μL per well), and cultivation was performed under an atmosphere of 37° C. and 5% $CO_2$ for 2 hours. After that, the medium was removed from the well, the well was washed twice with phosphate buffered physiological saline (PBS) and supplemented with a fresh medium (100 μL per well), and cultivation was continued until the total cultivation time reached 72 hours. After that, a WST Reagent (Dojindo Laboratories) was added (10 μL per well), and cultivation was continued under an atmosphere of 37° C. and 5% $CO_2$ for about 2 hours. From each well, the absorbance (Abs450) of light at a wavelength of 450 nm was measured, and the cell growth rate (% cell growth) was calculated based on the below-indicated mathematical equation. It should be noted that "Abs450 value of control" in the mathematical equation means an absorbance obtained from a well in which the above-mentioned cultivation has been performed using a culture liquid free of DTX.

% cell growth=[(Abs450 value after addition of sample liquid)−(Abs450 value of blank)]/ [(Abs450 value of control)−(Abs450 value of blank)]×100

Figure 1:
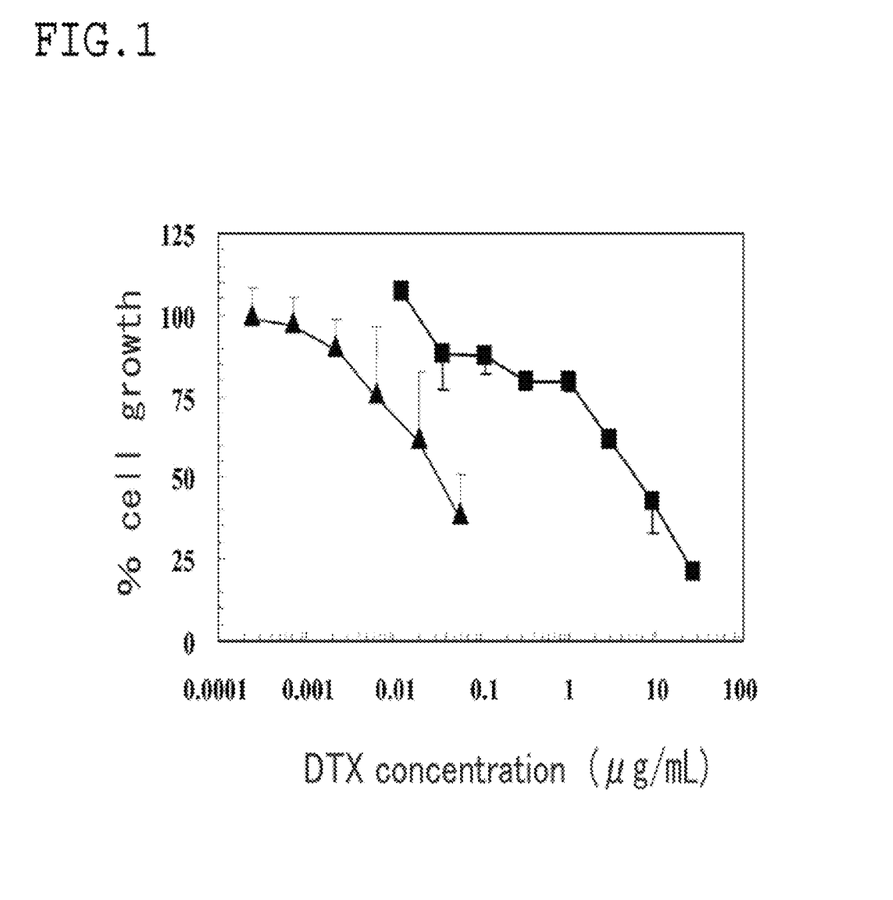
FIG. 1 is a graph for illustrating one example of data on a cancer cell damaging action of the polymer micelle of the present invention.

FIG. 1 is a graph illustrating a cell growth rate of an MDA-MB-231 cell against a docetaxel concentration. The horizontal axis in the graph represents a value of the amount of a micelle in a sample liquid expressed in a docetaxel concentration. Filled squares are data in the case of adding the Tf unbound DTX micelle, and filled triangles are data in the case of adding the Tf bound DTX micelle. The error bar in each data is a standard deviation (SD). As shown in the graph of FIG. 1, the cytotoxicity of the Tf bound DTX micelle on the MDA-MB-231 cell was exhibited from a remarkably low DTX concentration compared with that of the Tf unbound DTX micelle.

Cytotoxicity Test 2

In Cytotoxicity test 2, the cytotoxicity of each of the Tf bound DTX micelle in Example 2 and the Tf unbound DTX micelle in Comparative Example 1 was examined in the same manner as in Cytotoxicity test 1 except that the time of cultivation to be performed with addition of the sample liquid was changed to 72 hours, immediately after that, a WST Reagent was added in an amount of 10 μL per well, and cultivation was continued under an atmosphere of 37° C. and 5% $CO_2$ for about 2 hours.

The DTX concentration in each micelle was calculated based on the absorbance of light at a wavelength of 233 nm. The contribution of Tf (apo type) in the absorbance of light at a wavelength of 233 nm was subtracted in the case of the Tf bound DTX micelle.

Figure 2:
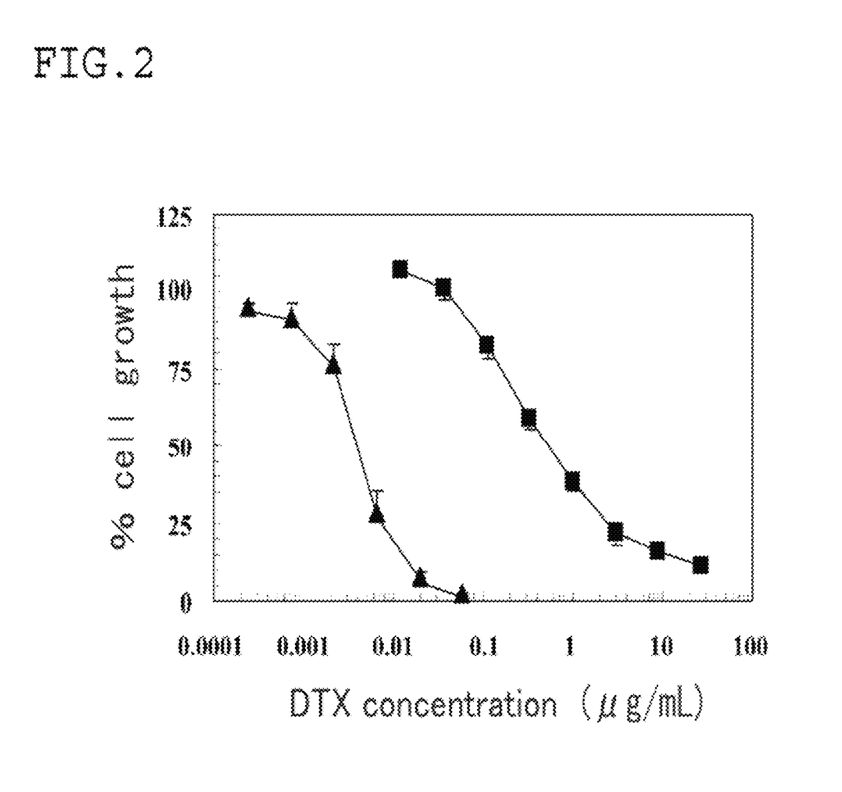
FIG. 2 is a graph for illustrating another example of data on a cancer cell damaging action of the polymer micelle of the present invention.

FIG. 2 is a graph illustrating a survival rate of an MDA-MB-231 cell against a docetaxel concentration. The longitudinal axis, horizontal axis, filled squares, and filled triangles in the graph have the same meanings as those in the graph of FIG. 1. The error bar in each data is a standard deviation (SD). As shown in the graph of FIG. 2, the cytotoxicity of the Tf bound DTX micelle on the MDA-MB-231 cell was exhibited from a remarkably low DTX concentration compared with that of the Tf unbound DTX micelle.

Cytotoxicity Test 3

In Cytotoxicity test 3, the cytotoxicity of each micelle was examined in the same manner as in Cytotoxicity test 1 except that a human prostate cancer DU145 cell purchased from American Type Culture Collection (ATCC) via Summit Pharmaceuticals International Corporation was used as the cell, and the Tf bound CPT micelle in Example 1 and the Tf unbound CPT micelle in Comparative Example 2 were used as the micelles, and the time of cultivation to be performed with addition of the sample liquid was changed to 8 hours.

Cytotoxicity Test 4

In Cytotoxicity test 4, the cytotoxicity of each micelle was examined in the same manner as in Cytotoxicity test 3 except that a human liver cancer HepG2 cell purchased from ECACC via DS Pharma Biomedical Co., Ltd. was used as the cell.

Cytotoxicity Test 5

In Cytotoxicity test 5, the cytotoxicity of each micelle was examined in the same manner as in Cytotoxicity test 3 except that a human breast cancer MDA-MB-231 cell was used as the cell.

Table 1 shows the results of Cytotoxicity tests 3 to 5. Data on "Solution" in Table 1 is data on the sample liquid prepared by directly adding CPT to a culture liquid without allowing CPT to be encapsulated in a micelle.

TABLE 1

| Cell name | Origin | GI50 (μg/mL) | | | Effect of Tf |
| --- | --- | --- | --- | --- | --- |
| | | Solution | Tf unbound micelle | Tf bound micelle | |
| DU145 | Human prostate cancer | 0.01 | 1.0 | 0.2 | 5.0 |
| HepG2 | Human liver cancer | 0.04 | 1.0 | 0.1 | 10.0 |
| MDA-MB-231 | Human breast cancer | 1.0 | 2.0 | 0.03 | 67.0 |

Effect of Tf: GI50 of Tf unbound micelle/GI50 of Tf bound micelle

The CPT concentration in each micelle was measured as follows.

a) Method for Measurement of CPT Concentration

To 100 μL of a micelle sample, 200 μL of 6 N HCl were added, and the mixture was heated in a cryotube (Ieda Chemical Co., Ltd.) at 100° C. for 1 hour. 75 μL of the obtained reaction liquid were recovered, neutralized with addition of 50 μL of 6 N NaOH, and then filtered through a 0.22-μm filter (MILLEX®-GV manufactured by Millipore Corporation). The filtrate was diluted 10-fold with a 25 mM ammonium formate buffer (pH 3.0), and the treated sample liquid was filled into an HPLC sample vial and measured for its CPT concentration by HPLC analysis under the following analysis conditions.

b) HPLC Analysis Conditions

System: Waters Alliance System
Column: Tosoh TSK-gel ODS-80TM (4.6Φ×150 mm) (40° C.)
Mobile phase: 25 mM ammonium formate (pH 3.0)/acetonitrile=70/30
Flow rate: 1 mL/min
Detection: fluorescence (Ex: 370 nm, Em: 420 nm)
Injection volume: 20 μL Cytotoxicity Test 6

In Cytotoxicity test 6, the cytotoxicity of each micelle was examined in the same manner as in Cytotoxicity test 3 except that a human breast cancer MDA-MB-231 cell purchased from ECACC via DS Pharma Biomedical Co., Ltd. was used as the cell, the Tf bound empty micelle in Comparative Example 3 was used as the micelle, and the contact time of a medicament and a cell was extended to 72 hours.

Figure 5:
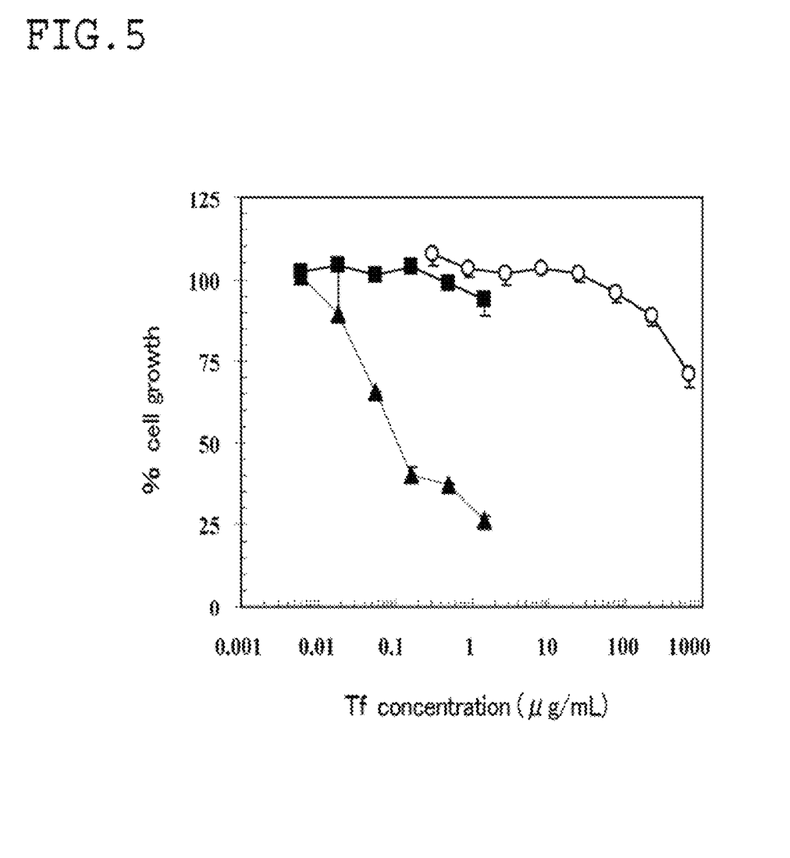
FIG. 5 is a graph for illustrating one example of data on a cancer cell damaging action of an active targeting polymer micelle that is free from a drug.

FIG. 5 is a graph illustrating a cell growth rate of an MDA-MB-231 cell against a Tf concentration. The horizontal axis in the graph represents a value of the amount of a micelle in a sample solution expressed in a Tf concentration. Filled squares are data in the case of adding the Tf bound empty micelle, filled triangles are data in the case of adding the Tf bound DTX micelle, and open circles are data in the case of adding the Tf solution. The error bar in each data is a standard deviation (SD). As shown in the graph of FIG. 5, the Tf bound docetaxel micelle exhibited excellent cytotoxicity on the MDA-MB-231 cell, while the Tf solution and the Tf bound empty micelle did not have cytotoxicity.

Medicinal Effect Evaluation Test

A human breast cancer MDA-MB-231 cell was cultivated by using a medium formed of RPMI1640 and 10% FBS under an atmosphere of 37° C. and 5% $CO_2$ until the number of growing cells reached the number of cells required for transplantation. After that, the cell was suspended in 100 μL of physiological saline, and inoculated into the dorsal subcutaneous tissue of a female nude mouse [Balb nu/nu, 5-week-old, manufactured by Charles River Laboratories Japan Inc.]. The number of cells inoculated per mouse is $3 \times 10^6$. After that, the nude mouse was fed for 21 days, and the administration of a micelle encapsulating a drug was started at the time when the tumor volume became $70.8 \pm 3.7$ mm$^3$ (Average±SE).

The administration schedule included intravenous administration via the tail vein in a total of 3 times every 4 days, and for the below-indicated 3 groups, the tumor volume and mouse body weight were measured 3 times a week. The number of mice was 8 for each group.

(1) Control (without treatment)
(2) Tf unbound DTX micelle in Comparative Example 1 (dose of DTX per administration: 10 mg per kg of mouse body weight)
(3) Tf bound DTX micelle in Example 2 (dose of DTX per administration: 10 mg per kg of mouse body weight)

Figure 3:
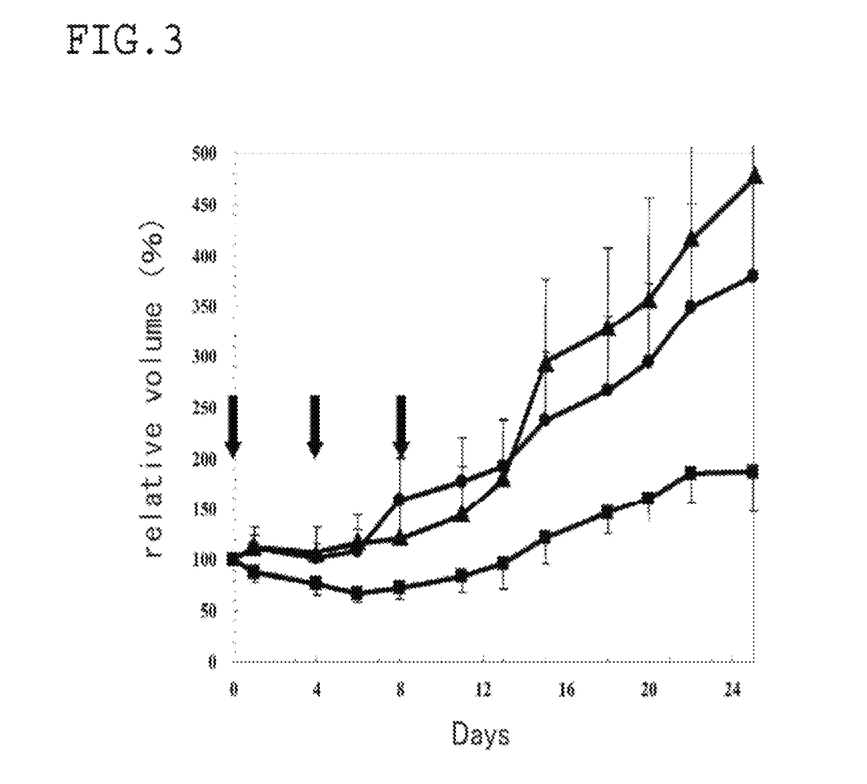
FIG. 3 is a graph for illustrating data on a temporal change in a tumor volume due to administration of the polymer micelle of the present invention.
Figure 4:
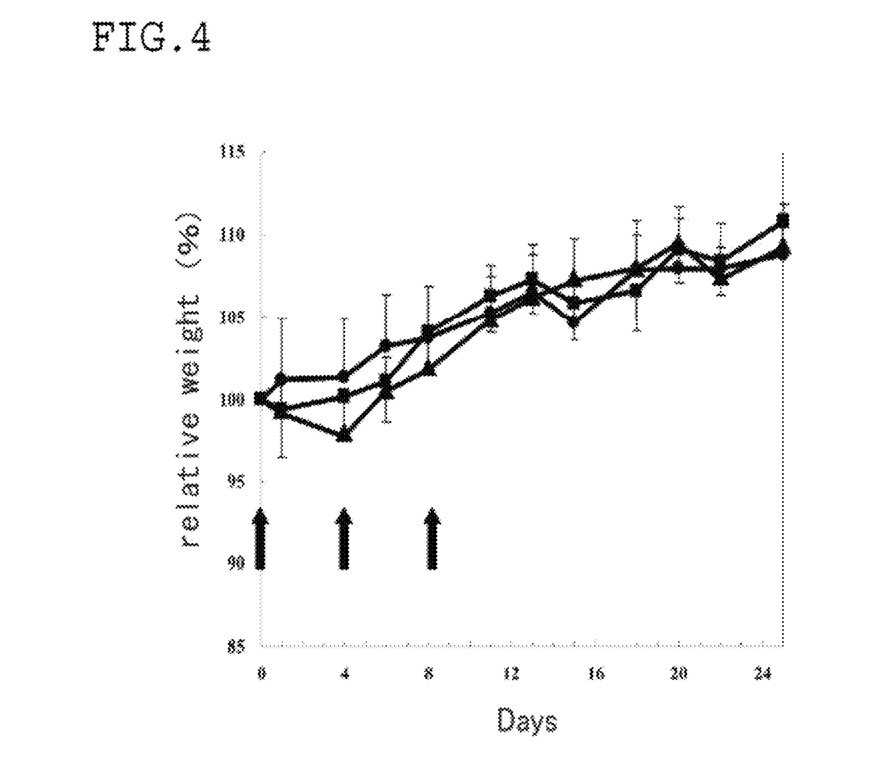
FIG. 4 is a graph for illustrating data on a temporal change in test animal body weight due to administration of the polymer micelle of the present invention.

FIG. 3 is a graph illustrating a time-dependent change in tumor volume. In the graph, the longitudinal axis represents relative values to the tumor volume at the start of the test, and the horizontal axis represents the elapsed time (Days) from the start of the test. In the graph, arrows each represent the timing at which a micelle encapsulating a drug has been administered. Filled circles are data for a control group, filled triangles are data for a Tf unbound DTX micelle group, and filled squares are data for a Tf bound DTX micelle group. FIG. 4 is a graph illustrating a change in mouse body weight. In the graph of FIG. 4, the longitudinal axis represents relative values to the mouse body weight at the start of the test. In graph of the FIG. 4, the horizontal axis, arrows, filled circles, filled triangles, and filled squares have the same meanings as those in the graph of FIG. 3. The error bar in each data is a standard error (SE).

As shown in the graphs in FIGS. 3 and 4, the administration of the Tf bound DTX micelle allowed the growth of the human breast cancer MDA-MB-231 cell to be remarkably suppressed without causing any difference in the change in mouse body weight, compared with the administration of the control and the Tf unbound DTX micelle. When the Tf bound DTX micelle was administered, the T/C value (tumor volume ratio of the drug treated group (T) and the control group (C)) could be reduced to 0.33 on Day 29 after administration, which was not shown in the graph of FIG. 3.

As used herein, the acronym "PBLA" stands for "poly(β-benzyl-L-aspartate)" and the acronym "pGlu" stands for "poly(α-glutamic acid)".

The invention claimed is:

1. A polymer micelle encapsulating a drug comprising:
a polymer α represented by the general formula I:

Z-A$_1$-B$_1$  (I); and a polymer β represented by the general formula II:

A$_2$-B$_2$(-D)  (II)

where: Z represents a residue of a compound having a target binding site; A$_1$ and A$_2$ each independently represent a hydrophilic segment of a polyethylene glycol chain; B$_1$ and B$_2$ each independently represent a hydrophobic segment of a polyamino acid chain; and D represents the drug with the proviso that one or more copies of the drug is (are) respectively covalently bound to one or more side chains of the polyamino acid chain of the polymer β, wherein when the polymer micelles collapse in blood, the polymer β is excreted through metabolism, to thereby prevent a normal cell from being damaged by the drug.

2. The polymer micelle according to claim 1, wherein the polymer α is represented by the following general formula I-a or I-b, and the polymer β is represented by the following general formula II-a or II-b:

(I-a)

(I-b)

(II-a)

(II-b)

where: R$_1$ represents the residue of the compound having the target binding site; R$_2$ represents a C$_1$ to C$_{12}$ alkyl group which may have a hydroxyl group at a terminus; L$_1$ represents O(CH$_2$)$_p$NH; L$_2$ represents O(CH$_2$)$_p$—CO—; p represents an integer ranging from 1 to 5; R represents a hydrogen atom or a hydrophobic organic group; q represents 1 or 2; n$_1$ and n$_2$ each independently represent an integer ranging from 40 to 450; m$_1$ and m$_2$ each independently represent an integer ranging from 20 to 80; R$_3$ represents a residue of the drug, provided that at least 10% to 70% of a total number m$_2$ may have a linker group; and if present, the rest group is a hydrogen atom or a hydrophobic organic group.

3. A pharmaceutical composition, comprising the polymer micelle according to claim 1 and a pharmaceutically acceptable carrier.

4. The polymer micelle according to claim 1, further comprising:
a polymer γ represented by the general formula III:

A$_3$-B$_3$  (III);

where: A$_3$ represents a hydrophilic segment of a polyethylene glycol chain, B$_3$ represents a hydrophobic segment of a polyamino acid chain, and the polymer γ is free of the target binding site and the drug.

5. The polymer micelle according to claim 1, wherein the polymer micelle contains no free drug.

6. The polymer micelle according to claim 1, wherein the target binding site comprises transferrin and the drug is docetaxel.

7. The polymer micelle according to claim 1, wherein the polyamino acid chain of the polymer α and the polymer β are each respectively and individually selected from polyglutamic acid, polyaspartic acid, ester derivatives thereof, amide derivatives thereof and salts thereof.

8. The polymer micelle according to claim 2, wherein n$_1$ and n$_2$ are 70-350.

9. The polymer micelle according to claim 8, wherein n$_1$ and n$_2$ are 110-280 and m$_1$ and m$_2$ are 25-50.

10. The polymer micelle according to claim 9, wherein the polyamino acid chain of the polymer α is comprised of poly (β-benzyl-L-aspartate), and the polyamino acid chain of the polymer β is comprised of poly(α-glutamic acid).

11. The polymer micelle according to claim 10, wherein the polymer micelle contains no free drug.

12. The polymer micelle according to claim 10, wherein the target binding site comprises transferrin and the drug is docetaxel.

13. The polymer micelle according to claim 1, wherein the target binding site comprises an F(ab')$_2$ fragment and/or an Fab fragment.

14. The polymer micelle according to claim 1, wherein the drug is selected from the group consisting of a nucleic acid derivative, temsirolumus and everolimus.

15. The polymer micelle according to claim 14, wherein the drug is gemcitabine.

16. The polymer micelle according to claim 15, wherein the target binding site comprises an $F(ab')_2$ fragment and/or an Fab fragment.

17. The polymer micelle according to claim 1, wherein the drug is selected from the group consisting of epothilone A, epothilone B, epothilone C, epothilone D, and derivatives thereof.

18. The polymer micelle according to claim 17, wherein the drug is epothilone B.

19. The polymer micelle according to claim 18, wherein the target binding site comprises an $F(ab')_2$ fragment and/or an Fab fragment.

20. A method of treating human breast cancer, comprising:
   administering a therapeutically effective amount of whole polymer micelles according to claim 1 to a patient in need thereof.

21. The polymer micelle according to claim 1, wherein the drug is bound to the polyamino acid chain via an ester bond or an amide bond.

\* \* \* \* \*

UNITED STATES PATENT AND TRADEMARK OFFICE
CERTIFICATE OF CORRECTION

PATENT NO. : 8,741,339 B2  
APPLICATION NO. : 12/672496  
DATED : June 3, 2014  
INVENTOR(S) : Yasuki Kato et al.

Page 1 of 1

It is certified that error appears in the above-identified patent and that said Letters Patent is hereby corrected as shown below:

On the title page item (73), the Assignee name should appear as follows:

(73) Assignee: NANOCARRIER CO., LTD.

Signed and Sealed this  
Thirtieth Day of September, 2014

Michelle K. Lee  
*Deputy Director of the United States Patent and Trademark Office*